US009846258B2

(12) United States Patent
Chen et al.

(10) Patent No.: US 9,846,258 B2
(45) Date of Patent: Dec. 19, 2017

(54) X-RAY BACKSCATTERING SAFETY INSPECTION SYSTEM HAVING A DISTRIBUTED-TYPE X-RAY SOURCE AND METHOD USING THE SAME

(71) Applicant: NUCTECH COMPANY LIMITED, Beijing (CN)

(72) Inventors: Zhiqiang Chen, Beijing (CN); Yuanjing Li, Beijing (CN); Ziran Zhao, Beijing (CN); Wanlong Wu, Beijing (CN); Yingkang Jin, Beijing (CN); Le Tang, Beijing (CN); Chengcong Xu, Beijing (CN); Ming Ruan, Beijing (CN); Guangwei Ding, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 115 days.

(21) Appl. No.: 14/792,066

(22) Filed: Jul. 6, 2015

(65) Prior Publication Data
US 2016/0003967 A1    Jan. 7, 2016

(30) Foreign Application Priority Data

Jul. 4, 2014    (CN) .......................... 2014 1 0317395

(51) Int. Cl.
*G01N 23/201*    (2006.01)
*G01V 5/00*    (2006.01)
*G01N 23/203*    (2006.01)

(52) U.S. Cl.
CPC ......... *G01V 5/0025* (2013.01); *G01N 23/203* (2013.01); *G01V 5/0066* (2013.01)

(58) Field of Classification Search
CPC .............. C12N 15/8274; C12N 9/0069; C12Y 113/11027; G01V 23/203; G01V 5/0025;
(Continued)

(56) References Cited

U.S. PATENT DOCUMENTS

| 4,750,196 A | 6/1988 | Harding |
| 5,600,700 A | 2/1997 | Krug et al. |

(Continued)

FOREIGN PATENT DOCUMENTS

| CN | 1947001 A | 4/2007 |
| CN | 102484935 A | 5/2012 |

(Continued)

OTHER PUBLICATIONS

European Patent Application No. 15175267.2; Extended Search Report; Dec. 2, 2015; 8 pages.

*Primary Examiner* — Irakli Kiknadze
(74) *Attorney, Agent, or Firm* — Baker & Hostetler LLP

(57) ABSTRACT

The present disclosure provides an X-ray backscattering safety inspection system, comprising: one or more backscattering inspection subsystem configured to inspect an object to be inspected by emitting X-ray beams towards the object to be inspected and inspecting scattering signals; and a control subsystem configured to adjust a distance between the backscattering inspection subsystem and locations on a side of the object to be inspected where are irradiated by the X-ray beams in real time according to a size of the object to be inspected such that the scattering signals inspected are optimized. The system may be adapted to objects to be inspected with different sizes or shapes while enhancing backscattering signals for imaging.

16 Claims, 3 Drawing Sheets

(58) Field of Classification Search
CPC .. G01V 5/0066; G01V 5/0016; G01V 5/0008; G01V 5/0041; G01V 5/005; G01V 5/0075; G01V 5/0033; G01V 5/0091; G01V 11/00; G01V 5/00; G01V 5/0058; G01V 3/10; G01V 3/104; G01V 3/105; G01V 5/0083; G01V 5/12; A61B 6/505; A61B 6/482; A61B 6/506; A61B 6/508; A61B 6/507; A61B 6/483; A61B 18/12; A61B 18/20; A61B 6/145; A61B 6/548; A61B 6/485; A61B 6/4021; A61B 6/4291; A61B 6/503; A61B 6/504; A61B 2503/40; A61B 5/415
USPC .................................................. 378/57, 86–90
See application file for complete search history.

(56) References Cited

U.S. PATENT DOCUMENTS

| | | |
|---|---|---|
| 6,421,420 B1 | 7/2002 | Grodzins |
| 6,459,764 B1 | 10/2002 | Chalmers et al. |
| 6,507,635 B2 * | 1/2003 | Birdwell ............... G01N 23/04 378/41 |
| 7,400,701 B1 * | 7/2008 | Cason ................. G01V 5/0025 378/57 |
| 2003/0016790 A1 | 1/2003 | Grodzins et al. |
| 2008/0253522 A1 * | 10/2008 | Boyden ................ G01N 23/201 378/87 |
| 2011/0019799 A1 | 1/2011 | Shedlock |
| 2012/0273684 A1 | 11/2012 | Akery |
| 2013/0039472 A1 * | 2/2013 | Morton ................ G01V 5/0041 378/88 |
| 2014/0185763 A1 | 7/2014 | Chen et al. |
| 2014/0185769 A1 | 7/2014 | Zhao et al. |

FOREIGN PATENT DOCUMENTS

| | | |
|---|---|---|
| CN | 202794067 U | 3/2013 |
| CN | 103063691 A | 4/2013 |
| CN | 103892853 A | 7/2014 |
| CN | 203981903 U | 12/2014 |
| EP | 1051609 B1 | 10/2005 |
| WO | WO 2012/174265 A1 | 12/2012 |

* cited by examiner

X-RAY BACKSCATTERING SAFETY INSPECTION SYSTEM HAVING A DISTRIBUTED-TYPE X-RAY SOURCE AND METHOD USING THE SAME

CROSS-REFERENCE TO RELATED APPLICATIONS

This application claims the benefit of Chinese patent application No. 201410317395.8, filed on Jul. 4, 2014 with State Intellectual Property Office of China, and the disclosures of which are incorporated herein in its entirety by reference.

BACKGROUND OF THE INVENTION

Field of the Invention

The present disclosure relates to a field of imaging by nuclear technique, and particularly to an X-ray backscattering safety inspection system having a distributed-type radiation source and a method using the same.

Description of the Related Art

A conventional X-ray safety inspection system for vehicles detects density difference of interior matters within the vehicle based on X-ray transmission principle. The conventional system represents good ability of identifying matters with medium or high density or great atomic number, but often misses matters with low density or small atomic number, such as explosive, drug, etc., because these materials have poor ability of blocking X-ray and thus the transmission image obtained has a rather poor contrast.

It is effective to inspect matters with low density or small atomic number within an object, such as contraband goods hidden in chassis or door of a vehicle, through X-ray backscattering imaging based on Compton Scattering principle on interaction between X-ray and matters.

The conventional X-ray backscattering safety inspection system emits spots-flying pencil-shaped X-ray beams through collimating on an object to be inspected and simultaneously receives backscattering signals from the object to be inspected by detectors located at the same side of the X-ray source and transforms them to electrical signals carrying position information, displaying the position and density difference of the object to be inspected on display screen.

Typically, an X-ray backscattering imaging inspection technology relates to single radiation source and image quality is in inverse property to the square of the distance between the vehicle and the detector. In order to cover the whole surface of the vehicle by the scanning X-ray while maintaining image quality, it is required that the distance between the vehicle and the detector is configured as small as possible and thus an emitting angle of the X-ray beams is very large. In this instance, uniformity of angular distribution of X-ray beams of a single source has to be good. In addition, the image formed by X-ray spot emitted at a great angle may be distorted, degrading image quality.

SUMMARY OF THE INVENTION

The present disclosure has been made to overcome or alleviate at least one aspect of the above mentioned disadvantages existing in the conventional technical solutions.

Accordingly, it is an object of the present disclosure to provide an X-ray backscattering safety inspection system having a distributed-type X-ray source.

According to a first aspect, there is provided an X-ray backscattering safety inspection system, comprising: a backscattering inspection subsystem, configured to inspect an object to be inspected by emitting X-ray beams towards the object to be inspected and inspecting scattering signals; and a control subsystem configured to adjust a distance between the backscattering inspection subsystem and locations on a side of the object to be inspected where are irradiated by the X-ray beams in real time according to a size of the object to be inspected such that the scattering signals inspected are optimized.

According to a second aspect, there is provided an X-ray backscattering passage-typed safety inspection system, comprising: a passage configured to be passed through an object to be inspected; a plurality of backscattering inspection subsystems disposed at at least two sides of the passage, the plurality of backscattering inspection subsystems being arranged to define the passage and each of the plurality of backscattering inspection subsystems being configured to emit X-ray beams to the object and inspect the object through inspecting scattering signals from the object; and, a control subsystem configured to adjust a distance between the backscattering inspection subsystems and locations on sides of the object where are irradiated by the X-ray beams in real time according to a size of the object such that the scattering signal inspected is optimized.

According to a third aspect, there is provided an X-ray backscattering passage-typed inspection method, comprising using the above mentioned safety inspection system to perform an inspection.

DETAILED DESCRIPTION OF THESE EMBODIMENTS

Figure 1:
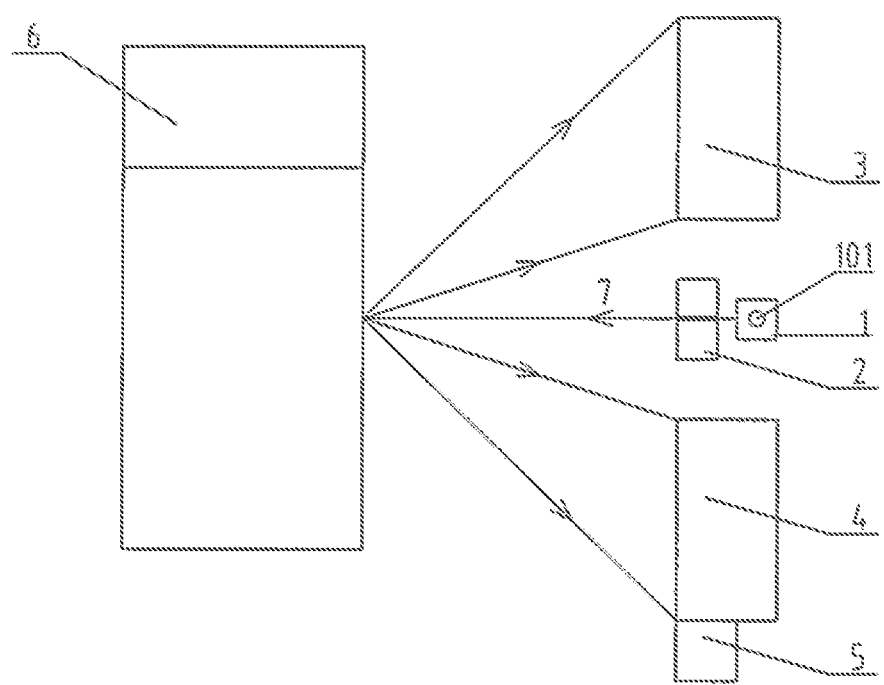
FIG. 1 is a schematic top view of an X-ray backscattering safety inspection system according to an embodiment of the present disclosure.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

According to an embodiment of the present disclosure, there is provided an X-ray backscattering safety inspection system, which includes a backscattering inspection subsystem configured to inspect an object to be inspected 6 by emitting X-ray beams towards the object to be inspected and inspect scattering signals. The X-ray backscattering safety inspection system also includes a control subsystem configured to adjust a distance between the backscattering inspection subsystem and locations on a side of the object to be inspected 6 where are irradiated by the X-ray beams in real time according to a size of the object to be inspected such that the scattering signals inspected are optimized.

The control subsystem may include a displacing device 8, which is used to displace the backscattering inspection subsystem in a direction orthogonal to a movement direction of the object to be inspected such that the distance between the backscattering inspection subsystem and the locations on a side of the object to be inspected where are emitted by the X-ray beams is adjustable.

The displacing device may include a guide rail 8, on which the backscattering inspection subsystem displaces.

The control subsystem may further include a distance measuring device 5 configured to measure a distance between the backscattering inspection subsystem and the locations on the side of the object to be inspected where are irradiated by the X-ray beams in real time.

The distance measuring device may include a telemetering component 5.

According to an embodiment of the present disclosure, the backscattering safety inspection subsystem may include an X-ray source 1. The X-ray source 1 may have a plurality of target spots that are individually controllable to emit X-rays. In the embodiment, the X-ray source 1 may be a distributed-type X-ray source including a plurality of target spots 101. The number of the target spots is not limited in any way.

Figure 2:
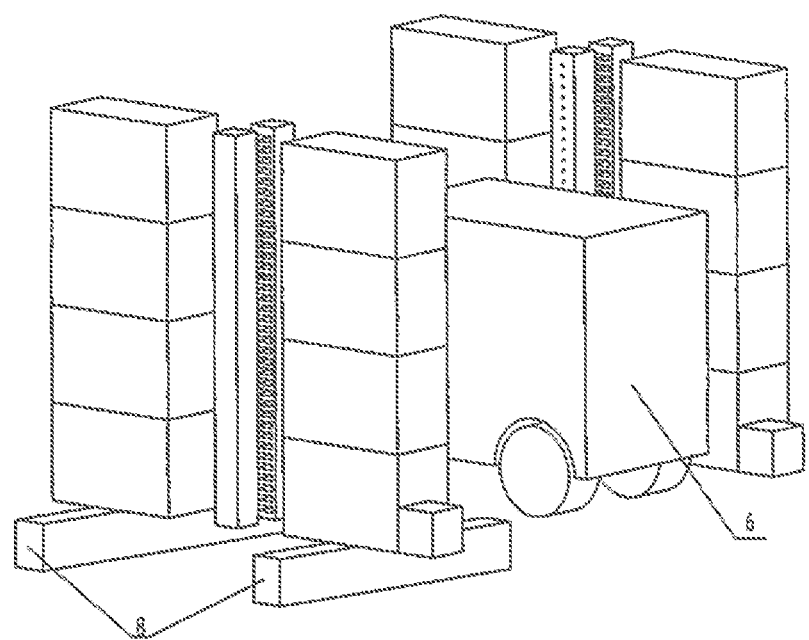
FIG. 2 is a schematic perspective view of an X-ray backscattering safety inspection system according to an embodiment of the present disclosure.

In the embodiment, the backscattering safety inspection subsystem may further include detectors 3 and 4 and collimator 2. FIG. 1 shows a top view of the backscattering inspection subsystem. FIG. 2 shows a perspective view of the X-ray backscattering passage-typed safety inspection system according to an embodiment of the present disclosure.

The plurality of target spots of the X-ray source 1 may be arranged in a linear manner. For example, preferably, the plurality of target spots of the X-ray source 1 may be arranged in a linear manner in vertical direction and each of the plurality of target spots may individually emit X-ray.

The control subsystem may control the target spots to individually emit X-ray in sequence and control the corresponding detector to receive the corresponding scattering signals. The control subsystem may further control the target spots to emit at one time and control the corresponding detectors to receive the corresponding scattering signals.

In the embodiment, each target spot 101 of the X-ray source 1 may be provided with a collimator 2 that is configured to modulate the X-rays. The collimator is located in front of the target spots such that the X-rays emitted from the target spots are passed through the collimator and then are outputted as at least one pencil-shaped X-ray beams, and the at least one pencil-shaped X-ray beams are irradiated onto at least one location of the object to be inspected 6.

The collimator 2 is configured such that the X-rays emitted from the target spot is collimated by the collimator 2 so as to output N pencil-shaped X-ray beams onto N locations on a side of the object to be inspected 6.

During a scan period, the collimator outputs N pencil-shaped X-ray beams and thus the object is actually scanned by the system for N times. The scanning results are integrated to produce enhanced inspection signals or increase inspection speed.

According to the embodiment of the present disclosure, alternatively, the control subsystem may be configured to process the scattering signals received by the detector and integrate the scattering signals of N scans to produce enhanced backscattering image or increase inspection speed.

In the case that the collimator outputs two pencil-shaped X-ray beams, the collimator is configured to output the two pencil-shaped X-ray beams in a horizontal plane and the angle between the two pencil-shaped X-ray beams is ranged from 10 degree to 150 degree such that the detectors may simultaneously receive the corresponding scattering signals with no crosstalk or negligible crosstalk.

According to the embodiment of the present disclosure, the control subsystem may be configured to adjust a distance between the backscattering inspection subsystem and locations on a side of the object that is irradiated by the X-ray beams such that they are located as close as possible to each other, facilitating the inspection.

In the embodiment, the system includes N detectors, which are configured to receive scattering signals from the object to be inspected irradiated by the N pencil-shaped X-ray beams.

According to the embodiment of the present disclosure, the control subsystem may be configured to adjust a distance between the backscattering inspection subsystem and locations on a side of the object to be inspected that is irradiated by the X-ray beams such that the detectors may detect scattering signals at sufficient intensity, thereby ensuring inspection being operated at an optimal position.

From this, the system according to the embodiment of the present disclosure may adjust the distance between the backscattering inspection subsystem and the object to be inspected in real time and emit X-ray beams in sequence or simultaneously by the plurality of target spots to irradiate the object to be inspected such that the system may achieve the scanning on the object by at least one X-ray beams during a completed scan period of the system.

Further, the system according to the embodiment of the present disclosure may adjust the distance between the backscattering inspection subsystem and locations on a side of the object to be inspected 6 where are irradiated by the X-ray beams in real time according to a size of the object to be inspected such that the backscattering inspection subsystem may always be located at the optimal position to emit X-ray beams and detect scattering signals, optimizing the inspection. In this instance, vehicles of any types may be inspected by the system according to an embodiment of the present disclosure when they are passing through the system. Even though an object having an abnormal shape is passed, the system according to an embodiment of the present disclosure may adjust a distance between the system and the surface of the object to be inspected in real time so as to inspect the object to be inspected.

Particularly, when a vehicle is moving through the passage, the control subsystem of the system according an embodiment of the present disclosure may move the backscattering inspection subsystem to adjust the distance between the backscattering inspection subsystem and locations on a side of the object to be inspected 6 where are irradiated by the X-ray beams in real time such that the backscattering inspection subsystem may always be located at the optimal position to perform the inspection while the distance between the backscattering inspection subsystem and the surface is changeable unceasingly. Accordingly, the adaptability and accuracy of the present system is largely increased.

The system according to the embodiment may be further configured to emit X-rays simultaneously by the plurality of target spots. It is appreciated that the operation of the target spots and sequence of emitting X-rays thereof may be configured as required. When an object having a planar surface is inspected, the control subsystem may firstly adjust a distance between the location on a surface of the object to be inspected and the backscattering inspection subsystem and then control the X-ray source to emit X-ray beams to the object to be inspected to perform the inspection.

According to the embodiment, the backscattering inspection subsystem may adjust a distance between the backscattering inspection subsystem and the locations on the surface of the object to be inspected where are irradiated by X-ray beams to obtain signals at best intensity for detecting, thereby producing a clear image.

According to the embodiment, when the object to be inspected passes through an inspection region, the control subsystem measures the distance between the backscattering inspection subsystem and the surface of the object to be inspected by a distance measuring device including a telemetering component and controls a movement of the backscattering inspection subsystem on the guide rail 8 so as to ensure that it emits pencil-shaped X-ray beams and detects the scattering signals at a suitable position. By scanning the object to be inspected, such as a vehicle, by X-ray beams and detecting scattering signals, a clear image may be obtained.

According to the embodiment, when a plurality of (for example, 2) X-ray beams are irradiated, the control subsystem may further integrate a movement speed of the object to be inspected, positions of the object to be inspected, etc., and the scattering signals from the two X-ray beams to obtain an enhanced backscattering image of the object to be inspected or increase scanning speed.

According to the embodiment, when two pencil-shaped X-ray beams are outputted simultaneously through a collimator from a target spot, they are preferably are arranged in a horizontal plane and are irradiated onto two locations on the object to be inspected, such as the vehicle 6, in a horizontal direction. Accordingly, there may have two detectors 3 and 4.

In the system according to the embodiment, an angle between the two pencil-shaped X-ray beams is preferably configured at a suitable angle as required. For example, the angle between the two pencil-shaped X-ray beams may be smaller than 180 degree, or smaller than 160 degree, or smaller than 150 degree, or smaller than 140 degree, or smaller than 130 degree, or smaller than 120 degree, or smaller than 110 degree, or smaller than 100 degree, or smaller than 90 degree, or smaller than 80 degree, or smaller than 70 degree, or smaller than 60 degree. The angle between the two pencil-shaped X-ray beams may be greater than 10 degree, or greater than 20 degree, or greater than 30 degree, or greater than 40 degree, or greater than 50 degree, or greater than 60 degree, or greater than 70 degree. For example, the angle between the two X-ray beams is configured as 60 degree such that the detectors 3 and 4 may receive corresponding scattering signals simultaneously with no crosstalk or negligible crosstalk. Based on the present disclosure, it is feasible to determine a suitable angle between the two pencil-shaped X-ray beams as required. In practice, as the volume and shape of object to be inspected is variously changeable and thus a distance between the surface of the object to be inspected and the target spots/collimator is changeable, it is advantage according to the present embodiment to provide the displacing device on the guide rail to adjust the distance such that the backscattering inspection subsystem is located in a suitable position in real time. For example, the subsystem is located as close as possible to the object. In this instance, the angle between the two X-ray beams may be adjusted in the above mentioned range as required.

The angle is limited by the flare angle of the two emitting beams with respect to the collimator and the distance between the subsystem and the object to be inspected. As the detectors and the X-ray source are arranged at the same side of the object, the angle between each of the emitting X-ray beams and the corresponding scattering beam is greater than 90 degree. The scattering process thus belongs to Compton Backscattering process.

In an embodiment, when more than two X-ray beams are irradiated, the irradiating angle may be configured as required. For example, in addition to two X-ray beams in the horizontal plane, an X-ray beam emitted upwards obliquely is added, thereby adding a third or even a fourth X-ray beams. The third X-ray beam is angled to the horizontal plane at an acute angle so as to obtain Compton Backscattering X-ray beams other than the X-ray beams in the horizontal plane.

In this instance, the vehicle 6 may be scanned by the back-scattering X-ray beams at least two times during one scan operation of the inspection system, which is favor of a succeeding image enhancing process and results in a better image based on enhanced back-scattering signals or increases a speed of the vehicle and thus reduces time for a completed scanning.

According to an embodiment of the present disclosure, there is provided an X-ray backscattering passage-typed safety inspection system, comprising a passage configured to be passed through an object to be inspected. The passage-typed safety inspection system further includes a plurality of backscattering inspection subsystems. In this embodiment, each of the backscattering inspection subsystems may be the backscattering inspection subsystem according to the above embodiment.

For example, the backscattering inspection subsystem may include an X-ray source 1 having a plurality of target spots that are controllable individually to emit X-rays. In the embodiment, the X-ray source 1 may be a distributed-type X-ray source including a plurality of target spots 101. The number of the target spots is not limited at any way.

The backscattering inspection subsystem may further include detectors 3 and 4 and collimators 2.

In an embodiment, several backscattering inspection subsystems may be combined to form a passage, i.e., a passage for inspection. The number and configurations of the backscattering inspection subsystems may be determined as required. For example, an X-ray backscattering passage-typed safety inspection system according to an embodiment of the present disclosure includes two backscattering inspection subsystems. The two backscattering inspection subsystems are disposed at either side of an object to be inspected so as to define a passage. The two backscattering inspection subsystems may simultaneously operate and may each emit X-rays in sequence so as to scan and inspect a respective half of the object to be inspected in a transverse section in a vertical plane in clockwise direction or in counter-clockwise direction, thereby increasing a scanning speed. For example, the system including two backscattering inspection subsystems may obtain a scanning speed that is two times of the speed of a system including one backscattering inspection subsystem. The transverse section is perpendicular to the movement direction of the object to be inspected.

The X-ray backscattering passage-typed safety inspection system according to the embodiment may include a control subsystem configured to adjust distances between the plurality of backscattering inspection subsystems and locations on a corresponding side of the object to be inspected that are irradiated by the X-ray beams according to a size of the object such that scattering signals are optimized.

Figure 3:
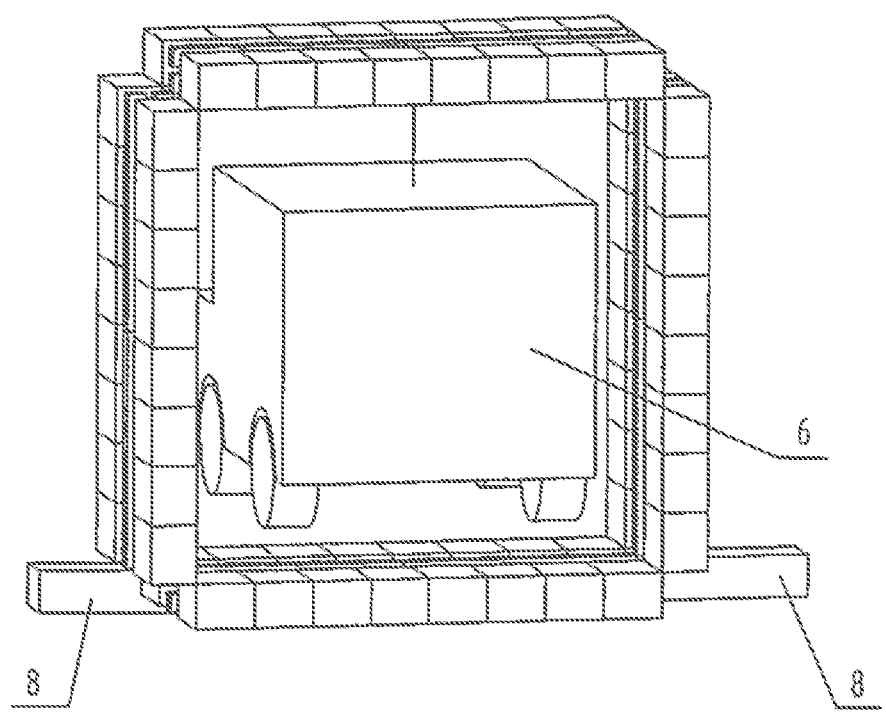
FIG. 3 is a schematic view of an X-ray backscattering passage-typed safety inspection system having four transmit-receive backscattering inspection subsystems according to an embodiment of the present disclosure.

Further, in the example shown in FIG. 3, the passage-typed safety inspection system includes four backscattering inspection subsystems that define a passage, thereby achieving a fast completed scan for a vehicle 6 from top, bottom and left, right. The control subsystem is configured to control movements of the backscattering inspection subsystems so as to adjust distances between the plurality of backscattering inspection subsystems and the object to be inspected. The passage-typed safety inspection system according to the embodiment may allow the vehicle 6 to pass the inspection area in constant speed while the control subsystem controls the movement of the backscattering inspection subsystems in real time so as to adjust the distances between the plurality of backscattering inspection subsystems and the object to be inspected.

According to the embodiment, the X-ray backscattering passage-typed safety inspection system includes X-ray sources each having a plurality of target spots that are individually controllable to emit X-rays.

The control subsystem of the inspection system according to the embodiment may control the backscattering inspection subsystems to operate in sequence or simultaneously, i.e., control the target spots to emit X-rays in clockwise direction or in counter-clockwise direction while controlling the detectors to receive the corresponding backscattering X-ray signals.

According to the embodiment, the backscattering inspection subsystems may further include collimators, each configured to be passed by X-rays emitted by the corresponding target spot and simultaneously output N pencil-shaped X-ray beams, and the N pencil-shaped X-ray beams irradiate N locations on the object to be inspected, and N detectors configured to receive the scattering signals from the object to be inspected, wherein N is a positive integral number.

The X-ray backscattering passage-typed safety inspection system according to the embodiment may scan locations on the vehicle 6 by the N pencil-shaped X-ray beams and thus obtain backscattering signals of N "sections" of the object to be inspected by a completed scanning. Further, the distance between the vehicle and the backscattering inspection subsystems may be adjusted in real time such that they are as close as possible to each other. After a continuous scanning, the scattering signals and the movement speed of the vehicle are integrated to obtain an image of one location on the vehicle, thereby achieving a completed scan of the vehicle 6 from top, bottom and left and right and improving a contrast of a backscattering image.

In the example shown in FIG. 3, when the vehicle passes the inspection passage, the control subsystem measures the distance between the corresponding backscattering inspection subsystem and the surface of the vehicle by a telemetering component and adjusts the distance to allow the corresponding backscattering inspection subsystem and the surface of the vehicle to be located as close as possible to each other. Meanwhile, the backscattering inspection subsystem at left side emits X-ray beams from bottom to top in sequence while the backscattering inspection subsystem at right side emits X-ray beams from top to bottom in sequence. Further, the detectors receive the corresponding scattering signals and output signals for imaging. The backscattering inspection subsystem at top side and the backscattering inspection subsystem at bottom side may operate in the same manner as those in either side. In this instance, due to cooperation of the four backscattering inspection subsystems, the system may achieve a completed scan of the object to be inspected in an one-fourth of a period time than the time a system including only one backscattering inspection subsystem spends. Thus, the passage-typed inspection system may achieve an increased scanning speed. A passage-typed inspection system including any transmit-receive backscattering inspection subsystems may achieve an increased scanning speed and thus a decreased scanning period time as each array module/backscattering inspection subsystem located around the object to be inspected may scan in the same speed. Particularly, even though the vehicle had an irregular side profile, the control subsystem may move the backscattering inspection subsystems in real time according to the side profile to be scanned such that the backscattering inspection subsystems are maintained to be located to the vehicle as close as possible and perform a scan on the object to be inspected.

The inspection system may be provided with two "L"-shaped transmit-receive modules/backscattering inspection subsystems. The two "L"-shaped transmit-receive modules/backscattering inspection subsystems may be configured to a quadrilateral surrounding an object to be inspected. Alternatively, two "L"-shaped transmit-receive modules/backscattering inspection subsystems may be configured to a "⊓" shape to surround an object to be inspected from the top and the left and the right.

According to an embodiment of the disclosure, an X-ray backscattering passage-typed safety inspection system operates as below.

When a vehicle 6 is passing through an inspection region at a constant speed, the system is activated.

The control subsystem controls distances between the top and two sides of the vehicle 6 and the backscattering inspection subsystems, obtaining suitable respective positions of the backscattering inspection subsystems.

The inspection system emits X-ray beams in sequence to scan the vehicle by the backscattering inspection subsystems.

The control subsystem 5 controls the detectors, according to the sequence in which the X-ray target spots emit, to collect corresponding scattering signals in sequence.

When the vehicle 6 has passed through the inspection region, the right side, left side, top side and bottom side of the vehicle have been scanned completely twice or more times by the X-ray beams. An enhanced image of the vehicle is displayed by processing the backscattering signals.

The inspection system according to embodiments of the present disclosure advantageously includes a backscattering inspection system having a distributed-type X-ray source, which effectively reduces space requirement of installation, expands scanning region of a vehicle, largely simplifies mechanical structure for spot-flying X-ray and further enhances quality of the scanning image.

The inspection system according to embodiments of the present disclosure may adjust positions of the backscattering inspection subsystem during the scanning, particularly the scanning on an object having a irregular profile, thereby increasing quality of the scanning image.

Although several exemplary embodiments have been shown and described, it would be appreciated by those skilled in the art that various changes or modifications may be made in these embodiments without departing from the principles and spirit of the present disclosure, the scope of which is defined in the claims and their equivalents.

What is claimed is:

1. An X-ray backscattering safety inspection system, comprising:

a backscattering inspection subsystem, configured to inspect an object to be inspected by emitting X-ray beams towards the object to be inspected and inspecting scattering signals, wherein the backscattering inspection subsystem further comprises:
an X-ray source including a plurality of target spots each controllable individually to emit X-rays and the X-ray source configured to emit X-rays in sequence or simultaneously by the plurality of target spots, collimators configured to be respectively passed through the X-rays emitted from the plurality of target spots and each outputting N pencil-shaped X-ray beams, and the N pencil-shaped X-ray beams being irradiated onto N locations of an object to be inspected, and
N detectors configured to respectively receive scattering signals from the corresponding locations of the object to be inspected, in which N is a positive integer that is greater than or equal to 1; and
a control subsystem configured to adjust a distance between the backscattering inspection subsystem and locations on a side of the object to be inspected where are irradiated by the X-ray beams in real time according to a size of the object to be inspected such that the scattering signals inspected are optimized, wherein,
the control subsystem further comprises a distance measuring device configured to measure a distance between the backscattering inspection subsystem and the locations on the side of the object to be inspected where are irradiated by the X-ray beams in real time.

2. The X-ray backscattering safety inspection system according to claim 1, wherein,
the control subsystem comprises a displacing device configured to displace the backscattering inspection subsystem in a direction orthogonal to a movement direction of the object to be inspected such that the distance between the backscattering inspection subsystem and the locations on the side of the object to be inspected where are irradiated by the X-ray beams is adjustable.

3. The X-ray backscattering safety inspection system according to claim 1, wherein,
the displacing device comprises a guide rail, on which the backscattering inspection subsystem displaces.

4. The X-ray backscattering safety inspection system according to claim 1, wherein,
the distance measuring device comprises a telemetering component.

5. The X-ray backscattering safety inspection system according to claim 1, wherein,
N scans on the object to be inspected are performed by irradiating the N pencil-shaped X-ray beams from the respective collimators onto the object to be inspected during a scan period, thereby results of the N scans are integrated so as to obtain an enhanced inspection signals or increased inspection speed.

6. The X-ray backscattering safety inspection system according to claim 5, wherein,
the control subsystem is configured to process the scattering signals received by the detector and integrate the scattering signals of the N scans on the object to be inspected, to obtain an enhanced inspection signals or increased inspection speed.

7. The X-ray backscattering safety inspection system according to claim 1, wherein,
the collimator is configured such that at least two pencil-shaped X-ray beams are arranged in a horizontal plane, wherein an angle between the at least two pencil-shaped X-ray beams is ranged from 10 degree to 150 degree such that the corresponding detector receives the corresponding scattering signals simultaneously with no crosstalk or negligible crosstalk.

8. An X-ray backscattering safety inspection method, wherein,
using the X-ray backscattering safety inspection system according to claim 1 to perform a safety inspection.

9. A X-ray backscattering passage-typed safety inspection system, comprising:
a passage through which an object to be inspected passes;
a plurality of backscattering inspection subsystems disposed at least two sides of the passage, the plurality of backscattering inspection subsystems being arranged to define the passage and each of the plurality of backscattering inspection subsystems being configured to emit X-ray beams to the object to be inspected and inspect the object to be inspected by inspecting scattering signals from the object to be inspected, wherein the backscattering inspection subsystems each comprise:
an X-ray source having a plurality of target spots that are controllable individually to emit X-rays and the X-ray source being configured to emit X-rays in sequence or simultaneously by the plurality of target spots, collimators configured to be respectively passed through the X-rays emitted from the plurality of target spots and each outputting N pencil-shaped X-ray beams, and the N pencil-shaped X-ray beams being irradiated onto N locations of an object to be inspected, and
N detectors configured to respectively receive scattering signals from the object to be inspected that is irradiated by the N pencil-shaped X-ray beams, in which N is a positive integer that is greater than or equal to 1; and
a control subsystem configured to adjust a distance between the backscattering inspection subsystems and locations on sides of the object to be inspected where are irradiated by the X-ray beams in real time according to a size of the object to be inspected such that the scattering signal inspected is optimized, wherein,
the control subsystem further comprises a distance measuring device configured to measure distances between the backscattering inspection subsystems and the locations on sides of the object where are irradiated by the X-ray beams in real time.

10. The X-ray backscattering passage-typed safety inspection system according to claim 9, wherein,
the control subsystem comprises a displacing device configured to displace the backscattering inspection subsystems in a direction orthogonal to a movement direction the object to be inspected such that the distances between the backscattering inspection subsystems and the locations on sides of the object to be inspected where are irradiated by the X-ray beams is adjustable.

11. The X-ray backscattering passage-typed safety inspection system according to claim 9, wherein,
the displacing device comprises a plurality of guide rails, on which the backscattering inspection subsystems displace.

12. The X-ray backscattering passage-typed safety inspection system according to claim 9, wherein,
the distance measuring device comprises a plurality of telemetering components.

13. The X-ray backscattering passage-typed safety inspection system according to claim 9, wherein, the plurality of backscattering inspection subsystems comprises two backscattering inspection subsystems that are configured to cooperatively and simultaneously scan and inspect at either side of the object in a vertical cross-section plane with respect to the object to be inspected by emitting X-ray beams in sequence in clockwise manner or in counter-clockwise manner around the periphery of the object to be inspected, and collect and integrate scattering signals so as to form a backscattering image for the object to be inspected.

14. The X-ray backscattering passage-typed safety inspection system according to claim 9, wherein, the plurality of backscattering inspection subsystems comprises four backscattering inspection subsystems located at top side, bottom side, right side and left side of the object and integrate and configured to be cooperated with each other to simultaneously scan respective parts of the object to be inspected, forming a backscattering image for the object to be inspected.

15. The X-ray backscattering passage-typed safety inspection system according to claim 9, wherein, during a scan period of the system, the system scans the object for N times by means of each of the collimators that outputs N pencil-shaped X-ray beams, so as to integrate the results from the N scans to obtain an enhanced inspection signals or increased inspection speed.

16. An X-ray backscattering passage-typed inspection method, wherein, using the X-ray backscattering safety inspection system according to claim 9 to perform a safety inspection.

* * * * *